(12) United States Patent
Kunz et al.

(10) Patent No.: US 8,647,882 B2
(45) Date of Patent: Feb. 11, 2014

(54) CHIRAL SELECTORS AND STATIONARY PHASES FOR SEPARATING ENANTIOMER MIXTURES

(75) Inventors: Franz-Rudolf Kunz, Gelnhausen (DE); Peter Richter, Karlstein (DE); Stefan Merget, Rodgau (DE); Roland Singer, Alzenau (DE); Thomas Mueller, Bruchkoebel (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/241,767

(22) Filed: Sep. 23, 2011

(65) Prior Publication Data

US 2012/0015443 A1  Jan. 19, 2012

Related U.S. Application Data

(62) Division of application No. 12/400,846, filed on Mar. 10, 2009, now Pat. No. 8,268,631.

(60) Provisional application No. 61/035,875, filed on Mar. 12, 2008.

(30) Foreign Application Priority Data

Mar. 10, 2008 (DE) .......................... 10 2008 013 500

(51) Int. Cl.
*G01N 30/02* (2006.01)
*C07C 205/00* (2006.01)

(52) U.S. Cl.
USPC .......................................... 436/161; 562/553

(58) Field of Classification Search
None
See application file for complete search history.

(56) References Cited

U.S. PATENT DOCUMENTS

2008/0038785 A1  2/2008 Konegawa et al.

FOREIGN PATENT DOCUMENTS

CN  101040053 A  9/2007

OTHER PUBLICATIONS

Schleimer et al. "Enantiomer separation by high-performance liquid chromatography on polysiloxane-based chiral stationary phases", J. Chromat. A, 1994, v. 679, pp. 23-34.*
"Silane Coupling Agents: Connecting Across Boundaries", Gelest Inc., 2006, http://www.gelest.com/goods/pdf/couplingagents.pdf.*
Michael Schleimer, et al., "Enantiomer separation by high-performance liquid chromatography on polysiloxane-based chiral stationary phases", Journal of Chromatography A, vol. 679, No. 1, XP-009115160, 1994, pp. 23-34.
Christopher J. Welch., "Evolution of chiral stationary phase design in the Pirkle laboratories", Journal of Chromatography A, vol. 666, No. 1/02, XP-000482399,1994, pp. 3-26.

(Continued)

Primary Examiner — Yelena G Gakh
(74) Attorney, Agent, or Firm — Oblon, Spivak, McClelland, Maier & Neustadt, L.L.P.

(57) ABSTRACT

Chiral selectors having α-unsubstituted β-amino acid derivatives of the structure:

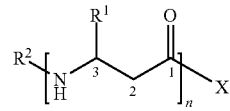

(I)

a stationary phase for separating substance mixtures containing the chiral selector, and processes for separating mixtures of chiral substances, including enantiomers, and especially enantiomers of substances selected from β-amino acids and derivatives thereof, α-amino acids and α-hydroxy acids are provided.

7 Claims, 4 Drawing Sheets

(56) References Cited

OTHER PUBLICATIONS

William H. Pirkle, et al., "An improved chiral stationary Phase for the facile separation of enantiomers", Journal of Chromatography, vol. 441, 1988, pp. 311-322.

William H. Pirkle, et al., "Improved chiral stationary phase for the separation of the enantiomers of chiral acids as their anilide derivatives", Journal of Chromatography, vol. 471, No. 1, Jun. 2, 1989, pp. 271-281.

G. Subramanian., "A Practical Approach to Chiral Separations by Liquid Chromatography", Weinheim. New York, Aug. 1994, 15 pages.

A. Kuhl, et al., "Alicyclic β-amino acids in Medicinal Chemistry", Amino Acids, vol. 29, 2005, pp. 89-100.

Yan Wang, et al., "Identification of Chiral Selector from a 200-Menber Parallel Combinatorial Library", Anal. Chem., vol. 72, No. 21, Nov. 1, 2000, pp. 5459-5465.

Ilaria D'Acquarica, et al., "Application of a new chiral stationary phase containing the glycopeptide antibiotic A-40,926 in the direct chromatographic resolution of β-amino acids", Tetrahedron: Asymmetry, vol. 11, 2000, pp. 2375-2385.

Gerald Gübitz, et al., "Chiral Separation by Chromatographic and Electromigration Techniques. A Review", Biopharmaceutics & Drug Disposition, vol. 22, 2001, pp. 291-336.

Gerald Gübitz, et al., "Methods in Molecular Biology", Chiral Separations, Methods and Protocols, Humana Press, Totowa, New Jersey, 12 pages.

Jun Haginaka, et al., "Chiral Separations by Capillary Electrophoresis Using Proteins as Chiral Selectors", Methods in Molecular Biology, vol. 243, chapters 15-18, pp. 291-336.

A. Sztojkov-Ivanov, et al., "Comparison of Separation Efficiency of Macrocylic Glycopeptide-Based Chiral Stationary Phases for the LC Enantioseparation of β-Amino Acids", Chromatographia, vol. 64, No. 1/2 Jul. 2006, pp. 89-94.

P. Madhavan, et al., "Validated Chiral LC Method for the Enantiomeric Separation of β-Amino-B-(3-Methoxyphenyl) Propionic Acid", Chromatographia, vol. 66, No. 3/4, Aug. 2007, pp. 243-246.

Dr. Eric Francotte., "Multiparalleles Chiral Separation Screening", Chromatographie, GIT Labor-Fachzeitschrift, May 2006, pp. 452-455.

Davankov, "Ligand Chromatography as a novel method for the investigation of mixed complexes: stereoselective effects in x-amino acid copper(II) complexes", Journal of Chromatography., vol. 60, 1971, pp. 280-283.

William H. Pirkle, et al., "Broad Spectrum Resolution of Optical Isomers Using Chiral High-Performance Liquid Chromatographic Bonded Phases", Journal of Chromatography, vol. 192, 1980, pp. 143-158.

A. Peter, et al., "High-performance liquid chromatographic enantioseparation of β-amino acids", Journal of Chromatography A., vol. 926, 2001, pp. 229-238.

Róbert Berkecz, et al., "High-Performance liquid chromatographic enantioseparation of β-amino acid stereoisomers on a (+)-(18-crown-6)-2,3,11,12-tetracarboxylic acid-based chiral stationary phase", Journal of Chromatography A., vol. 1125, 2006, pp. 138-143.

William H. Pirkle, et al., "Preparation of N-(2-Naphthyl)-2 amino Acids and Esters of High Enantiomeric Purity", J. Org. Chem., vol. 51, 1986, pp. 102-105.

Myung Ho Hyun, et al, "Preparation and evaluation of a doubly tethered chiral stationary phase based on (+)-(18-crown-6)-2,3,11,12-tetracarboxylic acid", J. Sep. Sci., vol. 28, 2005, pp. 421-427.

Istvan Ilisz, et al., "HPLC separation of amino acid enantiomers and small peptides on macrocyclic antibiotic-based chiral stationary phases: A review", J. Sep. Sci., vol. 29, pp. 1305-1321.

Veronika R. Meyer., "Praxis der Hochleistungs-Flüssigchromatographie", Wiley-VCH, 2004, 7 pages.

Michael Lämmerhofer, et al., "Recent developments in liquid chromatographic enantioseparation", Separation Methods in Drug Synthesis and Purification Handbook of Analytical Separations, vol. 1 Chapter 9, 2000, pp. 337-437.

Abstract from Henkel et al. "Substituted β-aminobutyric acid esters and salts", GB 776121, Oct. 19, 1955.

Chinese Office Action issued May 11, 2012 in patent application No. 200980108520.1 with English translation.

Combined Office Action and Search Report issued Oct. 19, 2012 in Chinese Patent Application No. 200980108520.1 with English language translation.

* cited by examiner (R,S)-3-tert-Butoxycarbonylamino-3-phenylpropionic acid (S)-3-tert-Butoxycarbonylamino-3-phenylpropionic acid (S)-3-tert-Butoxycarbonylamino-3-phenylpropionic acid after supplementation with 1% (R)-3-tert-butoxycarbonylamino-3-phenylpropionic acid

CHIRAL SELECTORS AND STATIONARY PHASES FOR SEPARATING ENANTIOMER MIXTURES

CROSS REFERENCE TO RELATED APPLICATIONS

This application is a divisional application of prior U.S. application Ser. No. 12/400,846, filed Mar. 10, 2009, the disclosure of which is incorporated herein by reference in its entirety. The parent application claims priority to German Application No. 102008013500.3, filed Mar. 10, 2008, and U.S. Provisional Patent Application 61/035,875, filed Mar. 12, 2008, the disclosures of which are incorporated herein by reference in their entireties.

BACKGROUND OF THE INVENTION

1. Field of the Invention

The present invention relates to the use of α-unsubstituted β-amino acids and especially derivatives thereof as chiral selectors for separating substance mixtures, preferably mixtures of chiral substances, more preferably enantiomer mixtures, especially enantiomers of substances selected from the group comprising β-amino acids and derivatives thereof, α-amino acids and α-hydroxy acids, and to chiral stationary phases (CSPs) which comprise α-unsubstituted β-amino acids and especially derivatives thereof as central chiral selectors, to their synthesis and to processes for separating substance mixtures, preferably mixtures of chiral substances, more preferably enantiomer mixtures, especially enantiomers of substances selected from the group comprising β-amino acids and derivatives thereof, α-amino acids and α-hydroxy acids with the aid of these stationary phases.

2. Discussion of the Background

The rising demand for enantiomerically pure substances and active ingredients for chemical and pharmaceutical applications has led to the development of a multitude of stereoselective separation technologies, in particular in the field of chromatography, which can be used either on the analytical scale for controlling enantiomeric purity and checking racemization processes, for pharmaceutical quality control and for pharmacokinetic studies, or on the preparative scale for providing enantiomerically pure compounds.

In contrast to diastereomers, enantiomers have identical chemical and physical properties in an achiral environment. Chromatographic enantiomer separations can therefore be carried out either using indirect methods, i.e. after reacting the analyte with a chiral derivatizing reagent to give a diastereomer mixture which, unlike an enantiomer mixture, can be separated on achiral phase material, or with the aid of so-called direct methods using a chiral selector which is incorporated into the mobile or stationary phase. The separating performance is based here on the different stability of the diastereomeric complexes which are formed by noncovalent interactions between the analyte and the selector.

Direct and also indirect processes have already found use in the field of enantiomer separation in various chromatographic and electrophoretic methods such as gas chromatography (GC), high-performance liquid chromatography (also high-pressure liquid chromatography, HPLC), thin-layer chromatography (TLC), super- and subcritical liquid chromatography (SLC), capillary electrochromatography (CEC) and capillary electrophoresis (CE) (Gübitz and Schmid (Eds.), Methods in Molecular Biology, Vol. 243: Chiral Separations: Methods and Protocols, Humana Press Inc: Totowa, N.J.: 2004; Gübitz and Schmid, Biopharm. Drug Dispos. 2001, 22, 291-336).

A derivatization of the analyte means at least one additional reaction step, which can lead to the formation of undesired by-products and decomposition products and to (partial) racemization. In addition, suitable functional groups must be present in the analyte for derivatization, and the chiral derivatizing reagent must be available in high enantiomeric purity (Gübitz and Schmid, Biopharm. Drug Dispos. 2001, 22, 291-336), which is why nonderivative direct chromatographic or electrophoretic methods are nowadays preferred. Although the addition of a chiral selector to the mobile phase of a chromatographic or electrophoretic system is a simple method for enantiomer separation in terms of handling, it is very expensive and not practicable in all cases.

Direct chromatographic processes using chiral stationary phases in which one chiral selector is bonded covalently or adsorptively to a support material are convenient in terms of handling and—assuming sufficient separating performance of the chiral phase material—also employable on the preparative scale. Specifically in the field of chiral stationary phases, a chiral selector which, on the one hand, allows an efficient separation of the two enantiomers of a chiral compound, but, on the other hand, is flexible enough to allow application for a wide class of compounds is desirable.

One variant of the direct methods is that of ligand exchange processes (LE), which are based on the formation of ternary mixed complexes between a metal ion, a chiral selector and the analyte, both of which function as ligands on the metal ion. What are responsible here for a successful separation are the different stability constants of the mixed complexes with the (R) and (S) enantiomers of the analyte. The ligand exchange principle has been used successfully for enantiomer separation in a number of the processes mentioned above: firstly with addition of a chiral selector to the electrolyte in capillary electrophoresis and secondly using chiral stationary phases in classical column chromatography, high-performance liquid chromatography, thin-layer chromatography and capillary electrochromatography, in which cases the chiral selector may be bonded covalently or adsorptively to the support material. Since, however, chiral separations cannot be forecast to the present day, it is still a great chromatographic challenge to find the suitable combination of chiral stationary and mobile phase efficiently and rapidly (Subramanian, Practical Approach to Chiral Separations by Liquid Chromatography, Wiley-VCH: Weinheim 1994; Gübitz and Schmid (Eds.), Methods in Molecular Biology, Vol 243: Chiral Separations: Methods and Protocols, Humana Press Inc: Totowa, N.J.: 2004; Francotte, GIT Labor-Fachzeitschrift May/2006, 452-455), and intensive studies have led to always novel and improved phase materials (Lämmerhofer and Lindner, In: Separation Methods in Drug Synthesis and Purification, Valkó (Ed.), Elsevier: Amsterdam 2000, 337-437). According to Armstrong et al. (Anal. Chem. 2001, 73, 557A-561A), as early as 2001, more than 100 chiral stationary phases based on different selectors were commercially available for high-performance liquid chromatography alone. Every manufacturer offers comprehensive application handbooks, in which the wide variety of different separating conditions, for example for aliphatic, aromatic, alicyclic or heterocyclic chiral amines, alcohols, amino alcohols or α-amino acids and derivatives thereof, are listed almost exclusively in a product-specific manner. This multitude of commercially available chiral stationary phases firstly demonstrates the immense significance and the great interest in these separation techniques, but also makes clear a great disadvantage which afflicts direct chromatographic and electrophoretic methods with the aid of chiral stationary phases to the present day: often, a series of (expensive) chiral stationary phases is needed to achieve an efficient separation even in the case of structurally closely related units.

Thus, in-house studies and also literature data demonstrate that, to date, a multitude of stationary phases which are then used in gas chromatography (GC) or liquid chromatography (for example HPLC) are needed for chiral chromatography, for example of β-amino acids and derivatives thereof. Conventionally known phases include, for example, cellulose carbamate phases, amylose derivatives, crown ethers (Berkecz et al., J. Chromatogr. A, 2006, 1125, 138-143; Hyun et al., J. Sep. Sci. 2005, 28, 421-427), ligand exchange phases (Hyun et al., J. Sep. Sci. 2003, 26, 1615-1622; Hyun et al., Biomed. Chromatogr. 2003, 17, 292-296) or macrocyclic glycopeptide phases (Sztojkov-Ivanov et al., Chromatographia 2006, 64, 89-94; Illisz et al., J. Sep. Sci. 2006, 29, 1305-1321 and literature cited there; D'Acquarica et al., Tetrahedron: Asymmetry 2000, 11, 2375-2385).

In the last few years, owing to their exceptional pharmacological properties, β-amino acids have been incorporated as key components into a multitude of peptidomimetics and further biologically active substances (Kuhl et al., Amino Acids 2005, 29, 89-100). Associated with this has also been the development of a rising demand for analytical methods for testing the enantiomeric purity of the synthesis units and end products, specifically also in the sector of minor trace determination for detection of traces of one enantiomer in the presence of a significant excess of the optical antipode (Juaristi and Soloshonok, Enantioselective Synthesis of β-Amino Acids, Wiley-VCH: New York 2005). It is an object of the present invention to provide novel chiral selectors, on the basis of which novel chiral phases for separating substance mixtures, preferably mixtures of chiral substances, more preferably enantiomer mixtures, especially enantiomers of substances selected from the group comprising β-amino acids and derivatives thereof, α-amino acids and α-hydroxy acids, can be provided, which allow efficient and very substantially universal separation of enantiomer pairs of chiral compounds, especially of β-amino acids and derivatives thereof, with chromatographic methods, especially with the aid of high-performance liquid chromatography, on the analytical and preparative scale.

It has now been found that, completely surprisingly, α-unsubstituted β-amino acid derivatives are flexible and nevertheless highly selective chiral selectors in processes for separating substance mixtures, preferably mixtures of chiral substances, more preferably enantiomer mixtures, especially β-amino acids and derivatives thereof. Further substance classes for which the selectors of the invention can be used for enantiomer separation are, for example, α-amino acid and α-hydroxy acids. It is thus a particular advantage of the present invention that the chiral phases which comprise chiral selectors based on α-unsubstituted β-amino acid derivatives are surprisingly usable universally for chromatographic separation of a large number of substance classes.

DETAILED DESCRIPTION OF THE INVENTION

Figure 1:
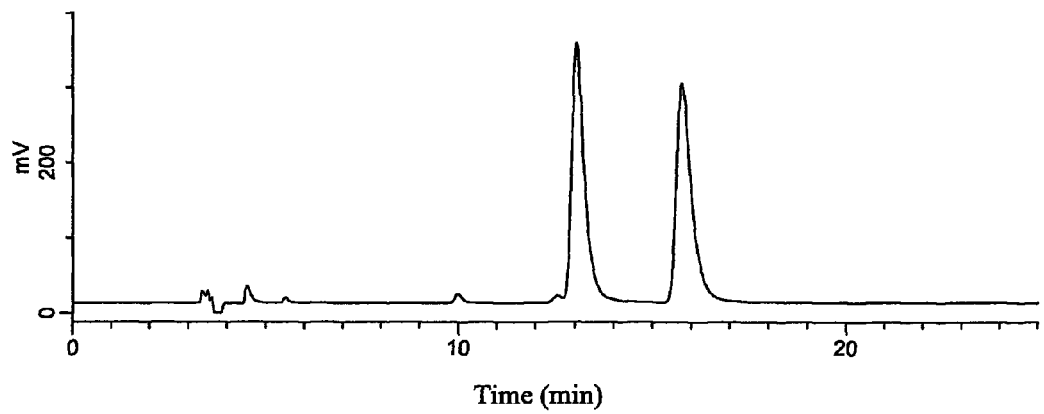
FIG. 1 shows the chromatographic resolution of optical isomers of different β-amino acid derivatives using chiral stationary phases according to Example 1.
Figure 1:
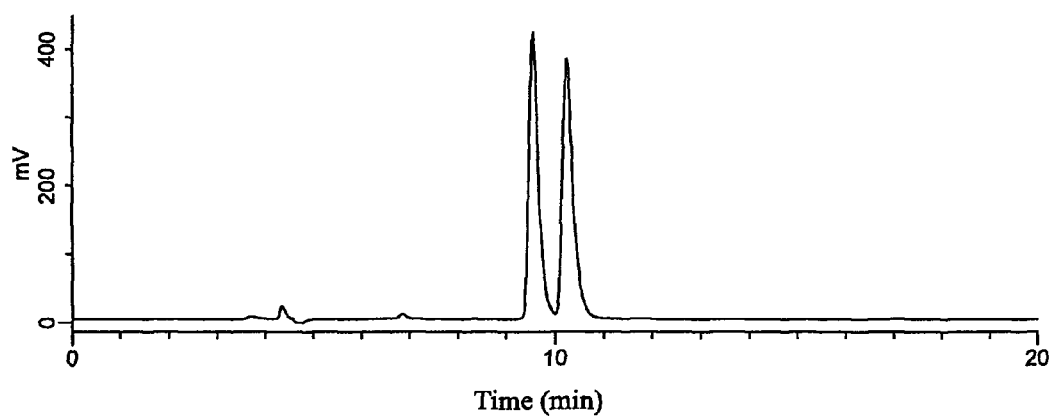
Figure 1:
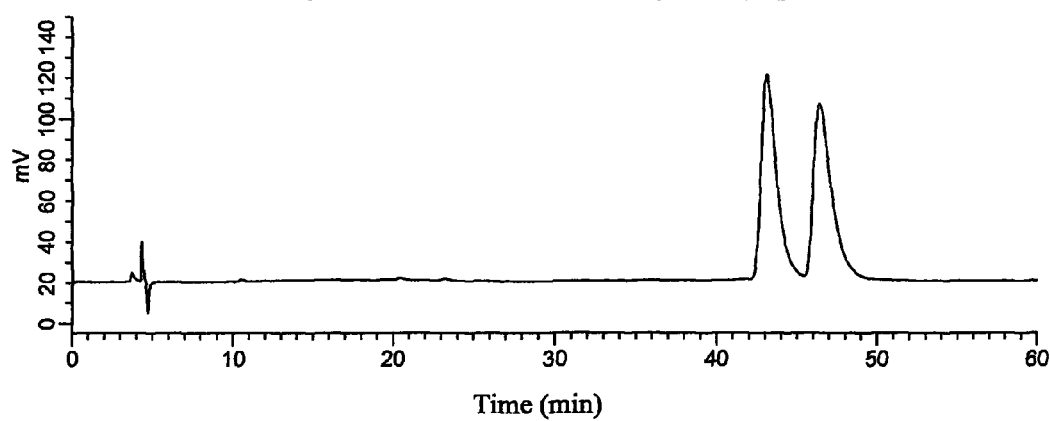

In one embodiment, the present invention therefore provides for the use of chiral selectors of the structure (I)

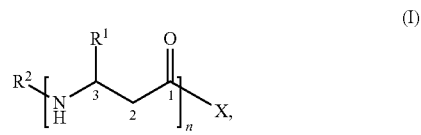

in which n=1-5, preferably n=1 or n=2, $R^1$=($C_1$-$C_4$)-alkyl, ($C_6$-$C_{10}$)-aryl, ($C_7$-$C_{13}$)-aralkyl, ($C_7$-$C_{10}$)-heteroaralkyl, pyridyl, hydroxymethyl, CH(OH)CH$_3$, CH$_2$CONH$_2$, CH$_2$COOH, (CH$_2$)$_2$CONH$_2$, (CH$_2$)$_2$COOH, (CH$_2$)$_4$NH$_2$, (CH$_2$)$_2$SCH$_3$ or (CH$_2$)$_3$NHC(NH)NH$_2$;
and $R^2$=3,5-dinitrobenzoyl or naphthyl when the chiral selector is attached covalently to a support material via a linker X, or $R^2$=CH$_2$CHR$^3$R$^4$ in which $R^3$=H or OH and $R^4$=($C_1$-$C_{20}$)-alkyl, ($C_6$-$C_{10}$)-aryl or ($C_7$-$C_{13}$)-aralkyl when X=OH.

According to the invention, the chiral selector is present predominantly in one absolute configuration with respect to the C3 carbon atom (β-carbon atom), while a stereocenter which is potentially present in the side chains need not be present in predominantly one absolute configuration.

In the context of the invention, a ($C_1$-$C_4$)-alkyl radical denotes a radical which has 1 to 4 saturated carbon atoms and may have any desired branches, preferably the methyl, isopropyl, isobutyl and sec-butyl radicals.

In the context of the invention, a ($C_6$-$C_{10}$)-aryl radical denotes an aromatic radical having from 6 to 10 carbon atoms, preferably the phenyl and 1- and 2-naphthyl radicals, which may be mono-, oligo-, poly- or persubstituted by further radicals or functional groups, especially by fluorine, chlorine, bromine, methyl and/or trifluoromethyl radicals, and hydroxyl and/or cyano groups.

In the context of the invention, a ($C_7$-$C_{13}$)-aralkyl radical preferably denotes a ($C_6$-$C_{10}$)-aryl radical bonded to the molecule via a methylene group, and additionally preferably phenylethyl and diphenylmethyl radicals.

In the context of the invention, a ($C_7$-$C_{10}$)-heteroaralkyl radical preferably denotes a pyridyl or indolyl radical bonded to the molecule via a methylene group.

In the context of the invention, a naphthyl radical preferably denotes a 1-naphthyl or 2-naphthyl radical, to which further substituents may be bonded.

In a preferred embodiment of the invention, $R^1$=phenyl; and in a particularly preferred embodiment, $R^1$=phenyl and n=1 or n=2. In a further preferred embodiment, $R^1$=phenyl, n=1 or n=2, and $R^4$=phenyl.

In a second embodiment, the invention further provides for the use of the chiral selectors described by structure (I) for preparing stationary phases for chromatographic separation processes of substance mixtures, preferably mixtures of chiral substances, more preferably enantiomer mixtures, especially enantiomers of substances selected from the group comprising β-amino acids and derivatives thereof, α-amino acids and α-hydroxy acids. According to this embodiment, the chiral selector may be bonded covalently or adsorptively to a support material based on silica gel or a monolith.

The chiral selectors described by structure (I) and the chiral stationary phases based thereon may be suitable as selectors in processes for chromatographically separating substance mixtures, preferably mixtures of chiral substances, more preferably enantiomer mixtures, especially enantiomers of substances selected from the group comprising β-amino acids and derivatives thereof, α-amino acids and α-hydroxy acids. As well as the enantiomer mixture, the sample may also comprise further compounds, for example by-products and/or impurities, which are to be removed. Chromatographic processes in the context of the invention include thin-layer chromatography (TLC), capillary electrochromatography (CEC), and more preferably high-performance liquid chromatography (HPLC). Further chromatographic processes in the context of the invention are micro-high-performance liquid chromatography (μ-HPLC) and capillary electrochromatography (CEC) on microchips (so-called lab-on-chip technology). A particular advantage of the present invention is that the chiral selectors allow the preparation of stationary phases which are stable under various conditions and can be operated in normal-phase mode (NP), or else in polar-organic mode (PO) and in reversed-phase mode (RP). A further advantage of the present invention is that the chiral selectors, owing to their high selectivity, allow the minor trace determination of enantiomers.

Preference is further given to the chromatographic processes mentioned in ligand exchange mode, in which the mobile phase comprises positively charged metal ions, preferably divalent metal ions, especially copper(II) ions (Davankov, J. Chromatogr. 1971, 60, 280-283). In the ligand exchange mode, preference is given to the adsorptive attachment of the chiral selector of the structure (I), where X=OH and $R^2$=$CH_2CHR^3R^4$ in which $R^3$=H or OH and $R^4$=($C_1$-$C_{20}$)-alkyl, ($C_6$-$C_{10}$)-aryl or ($C_7$-$C_{13}$)-aralkyl.

In a further embodiment, the invention provides a chiral stationary phase for chromatographic separation of substance mixtures, preferably mixtures of chiral substances, more preferably enantiomers, especially enantiomers of substances selected from the group comprising β-amino acids and derivatives thereof, α-amino acids and α-hydroxy acids, comprising a support material and a chiral selector, characterized in that the chiral selector is an α-unsubstituted β-amino acid derivative of the structure

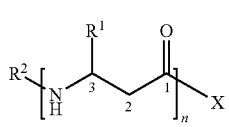

in which n=1-5, preferably n=1 or n=2, $R^1$=($C_1$-$C_4$)-alkyl, ($C_6$-$C_{10}$)-aryl, ($C_7$-$C_{13}$)-aralkyl, ($C_7$-$C_{10}$)-heteroaralkyl, pyridyl, hydroxymethyl, $CH(OH)CH_3$, $CH_2CONH_2$, $CH_2COOH$, $(CH_2)_2CONH_2$, $(CH_2)_2COOH$, $(CH_2)_4$—$NH_2$, $(CH_2)_2$—$SCH_3$ or $(CH_2)_3NHC(NH)NH_2$, $R^2$=3,5-dinitrobenzoyl or naphthyl, and X is a linker to the covalent attachment of the chiral selector to a support material.

According to the invention, the chiral selector may be present predominantly in one absolute configuration with respect to the C3 carbon atom (β-carbon atom).

Preferably, $R^1$=phenyl; and particular preference is given to the embodiment in which $R^1$=phenyl and n=1 or n=2.

The linker X may preferably be an aminoalkyl linker with a primary amino group, more preferably an aminopropyl linker, via which the selector is bonded to the support material as a carboxamide. This embodiment is shown in structure (II)

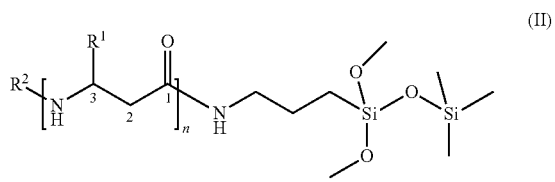

Preferred support materials in the context of the invention may be materials based on silica gel or monoliths.

In another embodiment, the invention further provides a process for preparing a chiral stationary phase comprising a chiral selector of the structure (I) or (II), comprising the following steps: (ia) acylating ($R^2$=3,5-dinitrobenzoyl) an α-unsubstituted β-amino acid or the corresponding β-amino acid ester with a 3,5-dinitrobenzoyl derivative suitable for acylation, preferably 3,5-dinitrobenzoyl chloride, or (ib) synthesizing an α-unsubstituted N-naphthylated β-amino acid or the corresponding β-amino acid ester ($R^2$=naphthyl) (ii) if esters were employed in (ia) or (ib), hydrolyzing the ester function, (iii) if n is greater than 1, coupling further α-unsubstituted β-amino acid units, and if the chiral selector is to be covalently attached to a support material, (iv) covalently attaching the chiral selector to a support material, via a linker. Compounds of the general structure (II) and (IIa) may be prepared, for example, by acylating ($R^2$=3,5-dinitrobenzoyl) the corresponding β-amino acid or the corresponding β-amino acid ester with a 3,5-dinitrobenzoyl derivative suitable for acylation, preferably 3,5-dinitrobenzoyl chloride (analogously to the process for preparing chiral phases, including those based on α-amino acids, published by Pirkle et al. (J. Chromatogr. 1980, 192, 143-158)). The synthesis of an α-unsubstituted N-naphthylated β-amino acid or of the corresponding β-amino acid ester in predominantly one enantiomeric form ($R^2$=naphthyl) may be possible, for example, through a variation of the classic Bucherer reaction proceeding from the corresponding β-amino acid and naphthol (analogously to the process for preparing N-(2-naphthyl)-2-amino acids and acid esters with high enantiomeric purities published by Pirkle and Pochapsky (J. Org. Chem. 1986, 51, 102-105)). The β-amino acid esters may be employed to form the selectors with a repetitive β-amino acid unit (n>1), which may be done, for example, by the route of classic peptide synthesis in solution. For details and alternative synthesis routes, reference is made to the relevant known literature concerning peptide synthesis (e.g. Houben-Weyl, Methoden der organischen Chemie [Methods of Organic Chemistry], Volume 15/1 and 15/2; M. Bodanszky, Principles of Peptide Synthesis, Springer Verlag 1984).

In a further additional embodiment, the invention provides a process for chromatographically separating substance mixtures, preferably mixtures of chiral substances, more preferably enantiomers, especially enantiomers of substances selected from the group comprising β-amino acids and derivatives thereof, α-amino acids and α-hydroxy acids, using the chiral selectors described by the structures (II) or (IIa) or the chiral stationary phases based thereon, comprising (i) contacting of a solution of the substance mixture to be separated with a chiral stationary phase comprising a support material and a chiral selector of the structure (II) or (IIa), (ii)

the separation of the individual constituents of the substance mixture on the basis of their different interaction with the stationary phase using a mobile phase and (iii) if isolation of the purified substances is sought, the fractional collection of the mobile phase and the isolation of the chromatographically purified substances therefrom. This process may additionally be suitable for minor trace determination of enantiomers, preferably of enantiomers of α- and β-amino acids. Preference may be given to liquid chromatography processes, especially HPLC processes. These may be carried out, for example, in normal-phase mode (NP), polar-organic mode (PO) or reversed-phase mode (RP) without addition of metal ions.

In addition, in a special embodiment, the present invention provides a chiral stationary phase for chromatographic separation of substance mixtures, preferably of mixtures of chiral substances, more preferably of enantiomers, especially of enantiomers of substances selected from the group comprising β-amino acids and derivatives thereof, α-amino acids and α-hydroxy acids, comprising a support material and a chiral selector, characterized in that the chiral selector is an α-unsubstituted β-amino acid derivative of the structure

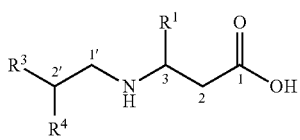

(III)

in which $R^1$=($C_1$-$C_4$)-alkyl, ($C_6$-$C_{10}$)-aryl, ($C_7$-$C_{13}$)-aralkyl, ($C_7$-$C_{10}$)-heteroaralkyl, pyridyl, hydroxymethyl, CH(OH)CH$_3$, CH$_2$CONH$_2$, CH$_2$COOH, (CH$_2$)$_2$CONH$_2$, (CH$_2$)$_2$COOH, (CH$_2$)$_4$—NH$_2$, (CH$_2$)$_2$—SCH$_3$ or (CH$_2$)$_3$NHC(NH)NH$_2$ and $R^3$=H or OH and $R^4$=($C_1$-$C_{20}$)-alkyl, ($C_6$-$C_{10}$)-aryl or ($C_7$-$C_{13}$)-aralkyl.

According to this special embodiment of the invention, the chiral selector may be present predominantly in one absolute configuration with regard to the C3 carbon atom (β-carbon atom), while the stereocenter potentially present in the 2' position need not be present in predominantly one absolute configuration.

In a preferred form of this special embodiment, $R^1$=phenyl.

In the context of this special embodiment, $R^4$ may preferably be a phenyl radical substituted by a short chain, more preferably an unsubstituted phenyl radical, or a linear or branched alkyl radical having 1 to 20 carbon atoms, preferably having 4 to 18 carbon atoms, more preferably having 6 to 16 carbon atoms, especially having 10 to 12 carbon atoms, and is more preferably n-decyl. In an especially preferred form of this embodiment, $R^1$=phenyl and $R^4$=n-decyl.

The chiral selectors of the formula (III) may be applied to suitable support materials preferably adsorptively by so-called dynamic coverage onto reversed-phase materials (RP materials), preferably based on silica gel or monoliths. Preferred RP materials are, for example, RP-2, RP-4, RP-5, RP-6, RP-8, RP-12 and especially RP-18.

In another embodiment, the invention further provides a process for preparing a chiral stationary phase comprising a chiral selector of the structure (III), comprising the following steps: (i) preparing the N-alkylated amino acid, and (ii) adsorptively attaching the N-alkylated amino acids to a support material.

The compounds of the general structure (III) may be prepared, for example, by reacting an appropriate epoxide compound with the particular β-amino acid using equimolar amounts of strong base, for example sodium methoxide (Busker et al., DE 3 143 726 A1). This leads to the racemic configuration at the 2' carbon atom. An alternative method of preparing chiral selectors of the structure (III) may be the N-alkylation of the appropriate β-amino acid with an n-alkyl bromide (for example according to Davankov et al., Chromatographia 1980, 13, 677-685).

In a further preferred embodiment of the invention, a process is provided for chromatographically separating substance mixtures, preferably mixtures of chiral substances, more preferably enantiomer mixtures, especially enantiomers of substances selected from the group comprising β-amino acids and derivatives thereof, α-amino acids and α-hydroxy acids, on the analytical, semipreparative or preparative scale, using the chiral selectors described by structure (III) or the chiral stationary phases based thereon, especially in ligand exchange mode (LE) with addition of metal ions, preferably divalent metal ions and more preferably copper(II) ions. Such a process comprises (i) the contacting of a solution of the substance mixture to be separated with a chiral stationary phase comprising a chiral selector of the structure (III), (ii) separating the individual constituents of the substance mixture on the basis of their different interaction with the chiral selector using a mobile phase comprising divalent transition metal ions, preferably copper(II) ions and (iii) in the case of a preparative or semipreparative liquid chromatography application, if appropriate the fractional collection of the mobile phase and the isolation of the chromatographically purified substance therefrom. This process may additionally be suitable for minor trace determination of enantiomers, preferably of enantiomers of α- and β-amino acids.

In the context of the invention, chromatographic separation refers to the separation of substance mixtures, preferably of mixtures of chiral substances, more preferably of enantiomer mixtures, especially of enantiomers of substances selected from the group comprising β-amino acids and derivatives thereof, α-amino acids and α-hydroxy acids, on a stationary phase, either for analytical purposes without subsequent isolation of the separated substances or for semipreparative or preparative purposes with subsequent isolation of the separated substances from constituents of the chromatographic system (support material, mobile phase) and other substances present in the sample.

In the context of the invention, in predominantly one absolute configuration means more than 50%, preferably at least 90%, especially at least 95%, of one optically active enantiomeric form, and more preferably the enantiomerically pure form.

As already mentioned, a multitude of chiral selectors and stationary phases based thereon are conventionally known. For example, for the separation of β-amino acids and derivatives thereof by means of high-performance liquid chromatography, chiral selectors based on crown ethers, α-amino acid derivatives or macrocyclic glycopeptides have been employed to date. Table 1 compares various chromatographic processes for separating enantiomeric β-amino acids which are conventionally known, and results which were achieved according to the present invention. The separating columns are characterized in a customary manner—as described, for example, in Meyer, Praxis der Hochdruckflüssigkeits-chromatogaphie [High-Pressure Liquid Chromatography in Practice], Wiley-VCH Weinheim 2004—by the capacity factors $k_1$ and $k_2$, the separation factor α and the resolution $R_s$. The exact chromatographic conditions can be taken from the particular original literature.

TABLE 1

Chromatographic separation of enantiomer mixtures of β-amino acids of the general structure $H_2N-CHR^1-CH_2-CO_2H$ on chiral stationary phases

| $R^1$ | Chiral selector | Mobile Phase* | $k_1$ | α | $R_s$ | Ref. |
|---|---|---|---|---|---|---|
| Ph | Vancomycin | MeOH/AcOH/TFA 100:0.1:0.1 | 0.70 | 1.13 | 0.80 | [1] |
| | (S)-Leucinol | MeOH/$H_2O$ 50:50 + $CuSO_4$ (0.3 mM) | 1.38 | 1.61 | 1.48 | [2] |
| | Ristocetin A | MeOH/AcOH/TFA 100:0.4:0.1 | 2.61 | 1.25 | 1.54 | [3] |
| | A-40,926 | MeOH/$H_2O$ 90:10 + $NH_4OAc$ (25 mM) | 0.71 | 1.33 | 2.03 | [4] |
| | Teicoplanin | MeOH/$H_2O$ 90:10 + $NH_4OAc$ (25 mM) | 0.73 | 1.32 | 2.05 | [4] |
| | (18-Crown-6)-2,3,11,12-tetracarboxylic acid | MeOH/$H_2O$ 50:50 + AcOH (5 mM) | 3.60 | 1.60 | 2.76 | [5] |
| | (R)-Phenylglycinol | MeOH/$H_2O$ 50:50 + $CuSO_4$ (0.3 mM) | 4.41 | 2.03 | 4.15 | [2] |
| | 3-Amino-3-phenyl-propionic acid | MeOH/$H_2O$ 90:10 + $Cu(OAc)_2$ (0.1 mM) | 3.16 | 1.72 | 5.08 | a |
| 3-MeOC$_6$H$_4$ | Teicoplanin | MeOH/AcOH/TFA 100:0.01:0.01 | 2.66 | 1.00 | 0.0 | [1] |
| | Vancomycin | MeOH/AcOH/TFA 100:0.1:0.1 | 0.75 | 1.16 | 0.80 | [1] |
| | Ristocetin A | MeOH/AcOH/TFA 100:0.1:0.1 | 1.43 | 1.15 | 1.00 | [1] |
| | (18-Crown-6)-2,3,11,12-tetracarboxylic acid | MeOH/$H_2O$ 50:50 + AcOH (5 mM) | 3.83 | 1.31 | 1.71 | [6] |
| | 4-(3,5-Dinitrobenzamido)-1,2,3,4-tetrahydrophenanthrene | n-Hexan/EtOH/TFA 90:10:0.2 | n.s.$^b$ | 2.6 | 2.1 | [7] |
| | 3-Amino-3-phenyl-propionic acid | MeOH/$H_2O$ 90:10 + $Cu(OAc)_2$ (0.1 mM) | 6.72 | 1.63 | 5.13 | a |
| 2-ClC$_6$H$_4$ | Teicoplanin | MeOH/AcOH/TFA 100:0.01:0.01 | 1.46 | 1.08 | <0.40 | [1] |
| | Ristocetin A | MeOH/AcOH/TFA 100:0.1:0.1 | 1.23 | 1.11 | 0.70 | [1] |
| | (18-Crown-6)-2,3,11,12-tetracarboxylic acid | MeOH/$H_2O$ 20:80 + (10 mM AcOH) | 3.04 | 1.14 | 1.06 | [6] |
| | 3-Amino-3-phenyl-propionic acid | MeOH/$H_2O$ 90:10 + $Cu(OAc)_2$ (0.1 mM) | 10.88 | 3.34 | 10.6 | a |

$^a$present invention;
$^b$n.s. = not specified
*further parameters: cf. literature/examples of this invention: flow rate 1 ml/min, 30° C.
[1] Sztojkov-Ivanov et al., Chromatographia 2006, 64, 89-94.
[2] Hyun et al., J. Sep. Sci. 2003, 26, 1615-1622.
[3] Péter et al., J. Chromatogr. A 2001, 926, 229-238.
[4] D'Acquarica et al., Tetrahedron: Asymmetry 2000, 11, 2375-2385.
[5] Hyun et al., J. Sep. Sci. 2002, 25, 648-652.
[6] Berkecz et al., J. Chromatogr. A 2006, 1125, 138-143.
[7] Madhavan, Chromatographia 2007, 66, 243-246.

As is evident from Table 1, the inventive selectors and the stationary phases based thereon are found to be exceptionally advantageous compared to the conventionally known selectors with regard to their separating performance, characterized by the separation factor α and the resolution of the enantiomers $R_s$, specifically also with regard to semipreparative and preparative applications. In addition, they exhibit wide applicability; reference is also made here to the results shown in Tables 2-4.

Chiral selectors which are based on α-amino acids have been described (II) (Welch, J. Chromatogr. A 1994, 3-26). However, none of the chiral selectors described there is an α-unsubstituted β-amino acid derivative. The results and significantly improved separation performance obtained according to the claimed invention are particularly surprising in view of stated conventional wisdom that a relatively great distance between the functional groups relevant for the chiral recognition and a relatively high conformational flexibility of the selector, which arise owing to the additional methylene group in the inventive selectors compared to α-amino acids or else compared to α-substituted β-amino acids, have an adverse effect on the separating performance (see, inter alia, Pirkle and McCune, J. Chromatogr. 1988, 441, 311; Wang et al., Anal. Chem. 2000, 72, 5459-5465; Welch, J. Chromatogr. A 1994, 3-26).

Having generally described this invention in the foregoing, a further understanding may be obtained by reference to certain specific examples which are provided herein for purposes of illustration only, and are not intended to be limiting, unless otherwise specified.

Example 1

Preparation of a Chiral Stationary Phase with Covalent Attachment of (S)-3-(3,5-dinitrobenzamido)-3-phenylpropionic Acid to an Aminopropyl-Functionalized Silica Gel Matrix (Amino Phase)

(1) Synthesis of (S)-3-(3,5-dinitrobenzamido)-3-phenylpropionic Acid 16 g of (S)-3-amino-3-phenylpropionic acid ((S)-β-phenylalanine) were admixed with 80 ml of 5% aqueous sodium hydroxide solution, and the resulting solution was adjusted to a pH of 11-12 by adding 50% aqueous sodium hydroxide solution. After adding 20 ml of tetrahydrofuran, the reaction mixture was cooled to 10° C., a solution of 23.1 g of dinitrobenzoyl chloride in 60 ml of tetrahydrofuran was added over a period of 60 min, and the reaction mixture stirred for a further 60 min. The organic phase was then removed by distillation, and the remaining aqueous phase extracted twice with methyl tert-butyl ether. The aqueous phase was admixed with 200 ml of ethyl acetate and adjusted to a pH of 1-2 by adding 4N hydrochloric acid. The phases were separated, and the organic phase washed with 200 ml of saturated sodium chloride solution. After the solvent was distilled off at 45° C. and p=150 mbar, the residue was taken up in 300 ml of cyclohexane. The product was filtered off and dried at 40° C. The product was purified further by means of preparative high-performance liquid chromatography on a reversed-phase material (e.g. Kromasil RP-18, particle size 10 μm) in an acetonitrile/water/trifluoroacetic acid solvent mixture. Yield: 8.0 g, HPLC purity 99.8 area %; elemental analysis: 53.4% C, 3.6% H, 12.7% N;

$^1$H NMR (DMSO) δ (ppm): 2.85 (dd, 1H), 2.96 (dd, 1H), 5.48 (m, 1H), 7.26 (t, 1H), 7.35 (t, 2H), 7.44 (d, 2H), 8.96 (t, 1H), 9.07 (d, 2H), 9.58 (d, 1H), 13.30 (s, 1H, $CO_2H$).

(2) Attachment of (S)-3-(3,5-dinitrobenzamido)-3-phenylpropionic Acid to an Aminopropyl-Functionalized Silica Gel Phase (Amino Phase)

4.1 g of amino phase (YMC-gel amino NH12S05, particle size 5 μm) were suspended in a solution of 4 g of (S)-3-(3,5-dinitrobenzamido)-3-phenylpropionic acid in 200 ml of tetrahydrofuran, and the reaction mixture was admixed with 3.2 g of N-ethoxycarbonyl-2-ethoxy-1,2-dihydroquinoline (EEDQ) with stirring. After 8 h at room temperature, the phase material was filtered off, washed with 50 ml each of methanol and diethyl ether and dried. Yield: 4.6 g of the desired support material, elemental analysis: 10.6% C, 1.2% H and 2.4% N; corresponding to a coverage of 0.4 mmol/g.

A 250×5 mm HPLC column was filled at 300 bar by the balanced-density method (see Meyer, Praxis der Hochdruckflüssigkeitschromatographie, Wiley-VCH: Weinheim 2004).

Application Example 1

The separating columns prepared according to Example 1 were suitable under HPLC conditions for chromatography of a multitude of β-amino acids or β-amino acid derivatives (Table 2). FIG. 1 shows the chromatographic resolution of optical isomers of different β-amino acid derivatives using separating columns according to Example 1.

TABLE 2

| Substance | Mobile Phase* | k'$_1$ | k'$_2$ | α | R$_s$ |
|---|---|---|---|---|---|
| 3-Acetylamino-3-(4-fluorophenyl)-propionic acid | A | 2.30 | 2.65 | 1.15 | 2.21 |
| 3-Acetylamino-3-(4-chlorophenyl)-propionic acid | A | 2.39 | 3.01 | 1.26 | 3.79 |
| 3-Acetylamino-3-(p-tolyl)propionic acid | A | 2.73 | 3.51 | 1.29 | 4.24 |
| 3-Acetylamino-3-(4-methoxyphenyl)-propionic acid | A | 4.71 | 6.41 | 1.36 | 5.52 |
| 3-Acetylamino-3-(4-nitrophenyl)-propionic acid | A | 4.59 | 5.00 | 1.09 | 1.30 |
| 3-Acetylamino-3-phenylpropionic acid | A | 3.12 | 3.71 | 1.19 | 2.77 |
| 3-tert-Butyloxy-carbonylamino-3-(4-fluorophenyl)propionic acid | B | 1.69 | 1.83 | 1.09 | 1.35 |
| 3-tert-Butyloxy-carbonylamino-3-(4-methoxyphenyl)propionic acid | B | 3.57 | 4.41 | 1.23 | 4.24 |
| 3-tert-Butyloxy-carbonylamino-3-(p-tolyl)propionic acid | B | 2.07 | 2.46 | 1.19 | 3.19 |
| 3-tert-Butyloxy-carbonylamino-3-(4-chlorophenyl)propionic acid | B | 1.73 | 1.93 | 1.11 | 1.85 |
| 3-tert-Butyloxy-carbonylamino-3-(4-nitrophenyl)propionic acid | B | 3.50 | 3.70 | 1.06 | 1.08 |
| 3-tert-Butyloxy-carbonylamino-3-phenylpropionic acid | B | 2.15 | 2.41 | 1.12 | 2.01 |
| 3-Benzyloxy-carbonylamino-3-(p-tolyl)propionic acid | B | 6.33 | 6.67 | 1.05 | 1.13 |
| 3-Benzyloxy-carbonylamino-3-(4-methoxyphenyl)propionic acid | B | 11.32 | 12.26 | 1.08 | 1.75 |

Mobile Phase A: Isohexane/ethanol/trifluoroacetic acid (800 + 200 + 1, v/v/v)
Mobile Phase B: Isohexane/methyl tert-butyl ether/ethanol/trifluoroacetic acid (800 + 150 + 50 + 1, v/v/v/v)
*further parameters: flow rate 1 ml/min, temperature 30° C.

Example 2

Preparation of a Chiral Stationary Phase with Covalent Attachment of (S)-3-[(S)-3-(3,5-dinitrobenzamido)-3-phenylpropanamido]-3-phenylpropionic Acid (3-(3,5-dinitrobenzoyl)-(S)-β-phenylalanyl-(S)-β-phenylalanine) to an Aminopropyl-Functionalized Silica Gel Matrix (Amino Phase)

(1) Synthesis of (S)-3-[(S)-3-(3,5-dinitrobenzoyl)-3-phenylpropanamido]-3-phenylpropionic Acid (3-(3,5-dinitrobenzoyl)-(S)-β-phenylalanyl-(S)-β-phenylalanine)

a. Synthesis of Ethyl (S)-3-(3,5-dinitrobenzamido)-3-phenylpropionate 11.49 g of ethyl (S)-3-amino-3-phenylpropionate hydrochloride were suspended in 100 ml of tetrahydrofuran and cooled to 0-10° C. in an icebath. After adding 14 ml of triethylamine, a solution of 11.52 g of 3,5-dinitrobenzoyl chloride in 40 ml of tetrahydrofuran was added with stirring and cooling over a period of 30 min. The cooling bath was removed, and the reaction mixture stirred for a further 120 min, in the course of which it warmed to room temperature. The reaction mixture was filtered, and the filtrate concentrated to dryness (product fraction 1). The filtercake—consisting of triethylamine hydrochloride and further product—was taken up in 100 ml of ethyl acetate and digested at 35° C. for 20 min. The suspension was filtered, and the filtercake discarded. The filtrate was concentrated to dryness under reduced pressure at 40° C. (product fraction 2). The product fractions were combined. Yield: 16.4 g; HPLC purity >97 area %. For further purification, the crude product was digested in 400 ml of water at room temperature for 2 h and then filtered. The moist yield was 15.4 g; HPLC purity 99.8 area %. The product was reacted further without further purification.

b. Hydrolysis to (S)-3-(3,5-dinitrobenzamido)-3-phenylpropionic Acid 15.4 g of ethyl (S)-3-(3,5-dinitrobenzamido)-3-phenylpropionate from reaction a were dissolved in 100 ml of tetrahydrofuran, and the resulting solution was admixed with 50 ml of water. With vigorous stirring, the slightly cloudy reaction mixture was heated to 45° C., and the pH was adjusted to 13-13.5 with 32% aqueous sodium hydroxide solution and kept constant for the course of the reaction. After the reaction ended (HPLC monitoring >99 area % conversion), the pH of the solution was adjusted to 7-8 by adding 6 N hydrochloric acid, then the organic solvent was distilled off under reduced pressure. The aqueous solution was diluted to 350 ml with water, and the pH was adjusted to 1-2 with 6 N hydrochloric acid with vigorous stirring. The precipitated product was filtered off with suction and washed twice with water. After drying at 40° C. under reduced pressure, a yield of 13.67 g was determined. The HPLC purity was 99.8 area %.

c. Synthesis of 2,5-dioxopyrrolidin-1-yl(S)-3-(3,5-dinitrobenzamido)-3-phenylpropionate (3-(3,5-dinitrobenzoyl)-(S)-β-phenylalanine 2,5-dioxopyrrolidin-1-yl Ester)

12 g of (S)-3-(3,5-dinitrobenzamido)-3-phenylpropionic acid from reaction b) were dissolved in 120 ml of tetrahydrofuran and admixed with 3.92 g of N-hydroxysuccinimide. With cooling in an icebath at 0-5° C., 7.1 g of dicyclohexylcarbodiimide was added in portions to the reaction mixture. On completion of addition, the mixture was left in the icebath with further stirring until the solution reached room temperature. After the reaction ended (HPLC monitoring >95 area % conversion), the precipitated dicyclohexylurea was filtered off and washed with tetrahydrofuran. The filtrate was concentrated under reduced pressure, and the residue digested at reflux in 250 ml of 2-propanol for 2 h. The product was filtered off with suction, washed with 2-propanol and dried at 50° C. under reduced pressure. The yield was 13.87 g; HPLC purity 98.8 area %.

d. Conversion to (S)-3-[(S)-3-(3,5-dinitrobenzamido)-3-phenylpropanamido]-3-phenylpropionic Acid (3-(3,5-dinitrobenzoyl)-(S)-β-phenylalanyl-(S)-β-phenylalanine)

5.65 g of (S)-3-amino-3-phenylpropionic acid were suspended in 70 ml of water, the pH of the suspension was adjusted to 10.5-11 by adding sodium hydroxide solution, and 70 ml of tetrahydrofuran were added. The mixture was cooled to 0-5° C. in an icebath and 13 g of 2,5-dioxopyrrolidin-1-yl(S)-3-(3,5-dinitrobenzamido)-3-phenylpropionate were added in portions with stirring over a period of 15 min. On completion of addition, the pH of the reaction mixture was kept between 9-9.5 by adding sodium hydroxide solution. On attainment of a constant pH with virtually full conversion (HPLC monitoring; <0.5 area % of reactant), the solution was diluted to a volume of about 800 ml with water, a pH of 1.5-2 was established by addling 4 N hydrochloric acid and the mixture was stirred for a further 30 min. The solid was filtered off with suction, washed with water and dried at 50° C. under reduced pressure. The dried solid was digested in 250 ml of tetrahydrofuran at 40° C. for 20 min, the suspension was cooled and the solid (product fraction 1) was filtered off with suction. The mother liquor was concentrated at a water bath temperature of 40° C. to a volume of about 70-80 ml, the resulting suspension was cooled to room temperature, and the solid (product fraction 2) filtered off with suction. The product fractions were combined and dried at 50° C. under reduced pressure. The yield was 11.1 g; HPLC purity >99.5 area %; $^1$H NMR (DMSO) δ (ppm): 2.64 (d, 2H), 2.77 (m, 2H), 5.15 (m, 1H), 5.52 (m, 1H), 7.10-7.20 (m, 5H), 7.25 (t, 1H), 7.31 (t, 2H), 7.39 (d, 2H), 8.44 (d, 1H), 8.95 (m, 1H), 9.01 (m, 2H), 9.53 (d, 1H), 12.17 (s, 1H, $CO_2H$).

(2) Attachment of the (S)-3-[(S)-3-(3,5-dinitrobenzamido)-3-phenylpropanamido]-3-phenylpropionic Acid to an Aminopropyl-Functionalized Silica Gel Phase (Amino Phase)

5 g of amino phase (YMC-gel amino NH12S05, particle size 5 μm) were suspended in a solution of 4.7 g of (S)-3-[(S)-3-(3,5-dinitrobenzamido)-3-phenylpropanamido]-3-phenylpropionic acid in 1 l of tetrahydrofuran, and the suspension admixed with 4 g of N-ethoxycarbonyl-2-ethoxy-1,2-dihydroquinoline (EEDQ) with stirring. After 24 h at room temperature, the phase material was filtered off, washed with 100 ml each of methanol and diethyl ether, and then dried. Elemental analysis: 12.44% C, 1.36% H and 2.76% N; corresponding to a coverage of 0.312 mmol/g.

A 250×5 mm HPLC column was filled at 300 bar by the balanced-density method (see Meyer, Praxis der Hochdruckflüssigkeitschromatographie, Wiley-VCH Weinheim 2004).

Application Example 2

The separating columns prepared according to Example 2 were also suitable under HPLC conditions for a multitude of β-amino acids or β-amino acid derivatives—in some cases with selectivity improved compared to the monomer. This is attributed to a more intense chiral recognition of the different analytes by the dipeptidic selector.

Figure 2:
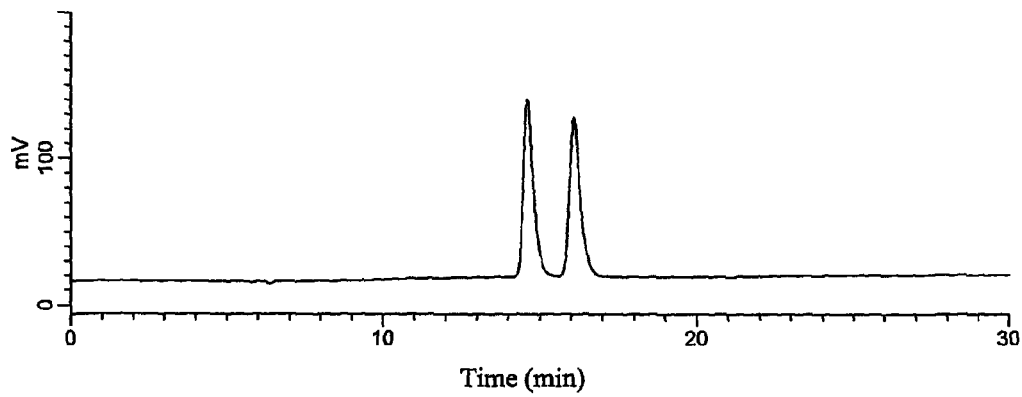
FIG. 2 shows the chromatographic resolution of optical isomers of different β-amino acid derivatives using chiral stationary phases according to Example 2.
Figure 2:
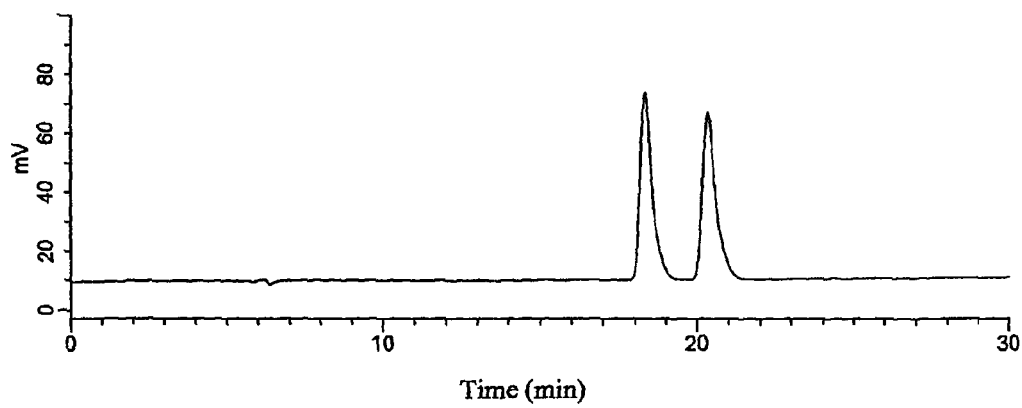
Figure 2:
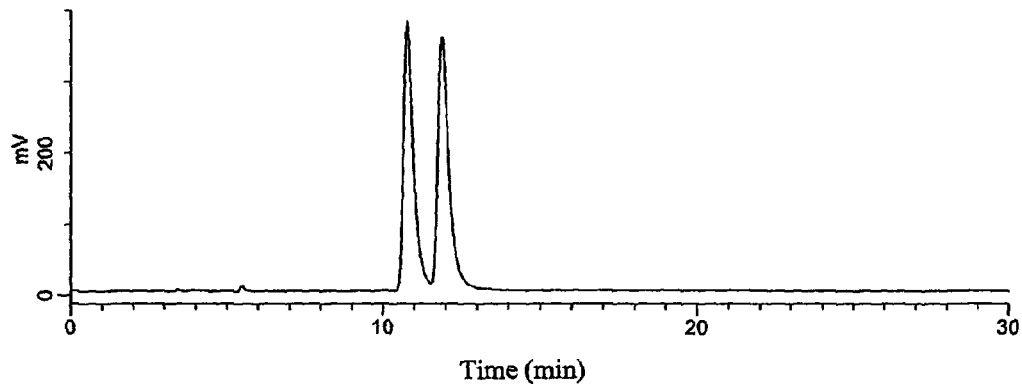
Figure 4:
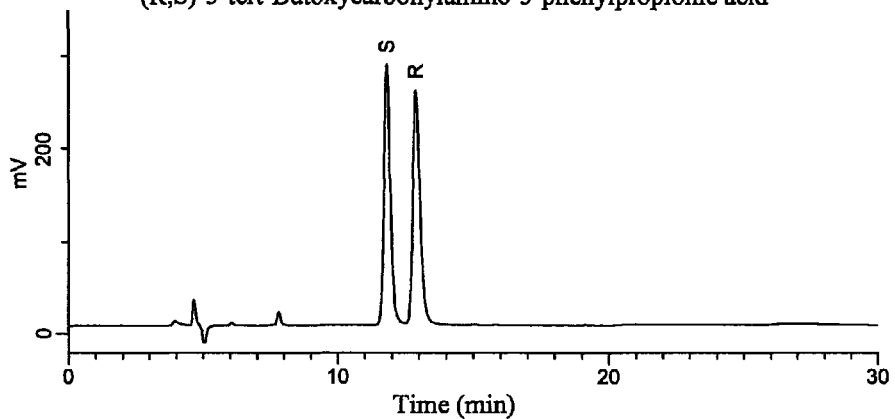
FIG. 4 shows the application use of a chiral stationary phase according to Example 2 for determining enantiomeric purity, especially in the field of minor trace determination.
Figure 4:
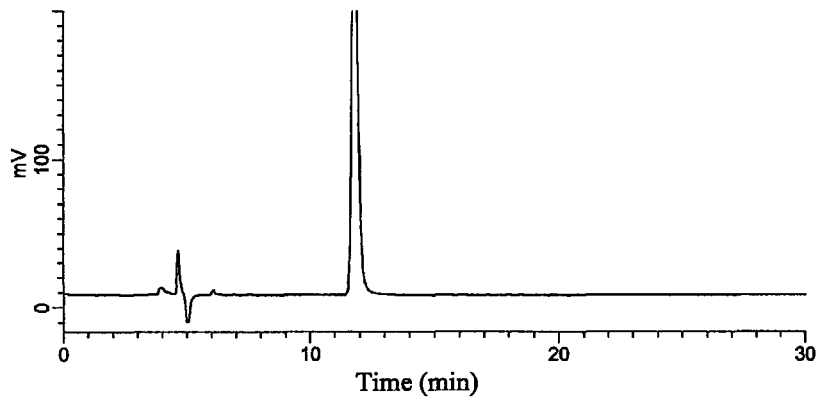
Figure 4:
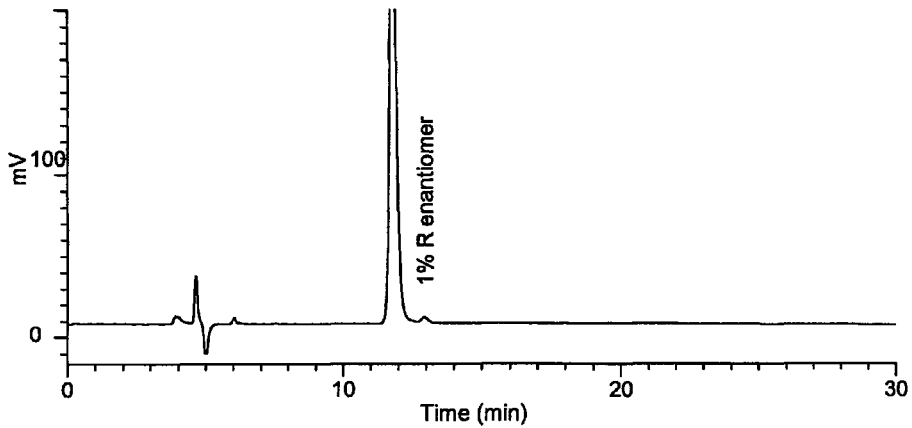

Table 3 summarizes the results. FIG. 2 shows the chromatographic resolution of optical isomers of different β-amino acid derivatives using the separating columns according to Example 2. FIG. 4 shows the application use of a chiral stationary phase according to Example 2 for determining enantiomeric purity, especially in the field of minor trace determination. The upper chromatogram shows the chromatographic resolution of a racemic mixture of (R)- and (S)-3-tert-butoxycarbonylamino-3-phenylpropionic acid using a chiral stationary phase according to Example 2. In the middle, the chromatogram of the pure (S)-3-tert-butoxycarbonylamino-3-phenylpropionic acid on this phase is shown. The lower chromatogram shows the resolution of (S)-3-tert-butoxycarbonylamino-3-phenylpropionic acid which has been supplemented with 1% (R)-3-tert-butoxycarbonylamino-3-phenylpropionic acid.

TABLE 3

| Substance | Mobile Phase* | k'₁ | k'₂ | α | R_s |
|---|---|---|---|---|---|
| 3-tert-Butyloxycarbonylamino-3-(4-fluorophenyl)propionic acid | A | 2.26 | 2.51 | 1.11 | 1.21 |
| 3-tert-Butyloxycarbonylamino-3-(4-methoxyphenyl)propionic acid | A | 4.52 | 5.85 | 1.29 | 2.64 |
| 3-tert-Butyloxycarbonylamino-3-(p-tolyl)propionic acid | A | 2.46 | 3.02 | 1.23 | 2.35 |
| 3-tert-Butyloxycarbonylamino-3-(4-chlorophenyl)propionic acid | A | 2.33 | 2.72 | 1.17 | 1.74 |
| 3-tert-Butyloxycarbonylamino-3-(4-nitrophenyl)propionic acid | A | 5.39 | 5.97 | 1.11 | 1.03 |
| 3-Benzyloxycarbonylamino-3-(p-tolyl)propionic acid | B | 1.50 | 1.70 | 1.14 | 2.04 |
| 3-Benzyloxycarbonylamino-3-(4-methoxyphenyl)propionic acid | B | 1.52 | 1.77 | 1.17 | 2.50 |
| 3-Benzyloxycarbonylamino-3-(4-fluorophenyl)propionic acid | B | 1.61 | 1.76 | 1.11 | 1.68 |
| 3-Benzyloxycarbonylamino-3-(4-chlorophenyl)propionic acid | B | 2.17 | 2.51 | 1.16 | 2.74 |
| 3-Benzyloxycarbonylamino-3-phenylpropionic acid | B | 1.21 | 1.33 | 1.10 | 1.33 |
| 3-Acetylamino-3-(4-fluorophenyl)propionic acid | C | 2.02 | 2.22 | 1.10 | 1.24 |
| 3-Acetylamino-3-(4-chlorophenyl)propionic acid | C | 2.08 | 2.40 | 1.15 | 1.82 |
| 3-Acetylamino-3-(p-tolyl)propionic acid | C | 2.22 | 2.63 | 1.19 | 2.40 |
| 3-Acetylamino-3-(4-methoxyphenyl)propionic acid | C | 3.76 | 4.58 | 1.22 | 2.85 |
| 3-Acetylamino-3-phenylpropionic acid | C | 2.31 | 2.62 | 1.13 | 1.66 |

Mobile Phase A: Isohexane/2-propanol/trifluoroacetic acid (900 + 100 + 1, v/v/v)
Mobile Phase B: Acetonitrile/water/acetic acid (700 + 300 + 1, v/v/v)
Mobile Phase C: Isohexane/ethanol/trifluoroacetic acid (750 + 250 + 1, v/v/v)
*further parameters: flow rate 1 ml/min, temperature 30° C.

Example 3

Preparation of a Chiral Stationary Phase with Dynamic Coverage of an RP Support Material with (3S)-3-(2-(R,S)-hydroxydodecylamino)-3-phenyl-propionic Acid (1) Synthesis of (3S)-3-(2-(R,S)-hydroxydodecy-lamino)-3-phenylpropionic Acid 27.01 g of sodium methoxide and 82.6 g of (S)-3-amino-3-phenylpropionic acid were dissolved in 800 ml of methanol. After adding 92 g of 1,2-epoxydodecane, the solution was stirred at room temperature for 20 h. Subsequently, the pH of the solution was adjusted to pH 6 with methanolic hydrochloric acid and the sodium chloride which crystallized out filtered off. After the methanol was distilled off, an oily residue remained, which crystallized in the course of stirring with 700 ml of acetone. This resulted in 153.4 g of colorless crystals. ¹H NMR (DMSO) δ (ppm): 0.85 (t, 3H), 1.13-1.31 (m, 18H), 2.28/2.60/2.70/2.86 (m, 2H), 3.02 (m, 1H), 3.34 (m, 1H), 3.66-3.78 (m, 1H), 4.57 (m, 1H), 5.20/5.29 (s, br., 1H, OH), 7.42 (m, 3H), 7.60 (m, 2H), 9.40 (s, br., 2H, NH₂⁺), 12.56 (s, 1H, CO₂H)

(2) Dynamic Coverage of an RP18 Support Material 1 g of (3S)-3-(2-(R,S)-hydroxydodecylamino)-3-phenylpropionic acid were dissolved in 50 ml of methanol (selector solution), and the stationary phase to be covered (Kromasil C18, column length 250 mm, internal column diameter 4.6 mm) was rinsed with methanol. Subsequently, the selector solution was pumped through the column with recycling with a flow rate of 1 ml/min for 3 h. After a methanolic rinse step at a flow rate of 4 ml/min, a saturated methanolic copper(II) acetate solution was pumped through the column at room temperature and a flow rate of 1 ml/min for about 30 min. Thereafter, the separating column was prepared for chromatographic use.

Application Example 3

The separating columns modified according to Example 3 were suitable in ligand exchange mode for enantiomer separation for a multitude of β-amino acids and derivatives thereof, but also α-amino acids and α-hydroxy acids.

Figure 3:
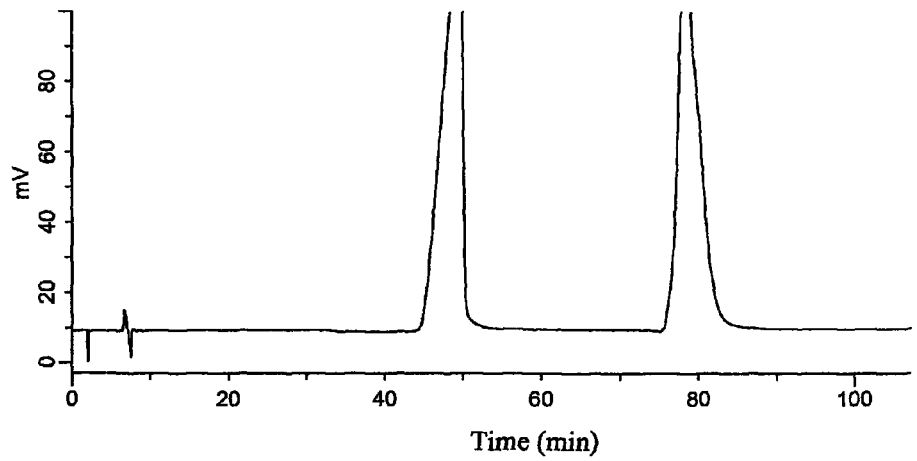
FIG. 3 shows the chromatographic resolution of optical isomers of different α- and β-amino acids and α-hydroxy acids using chiral stationary phases according to Example 3.
Figure 3:
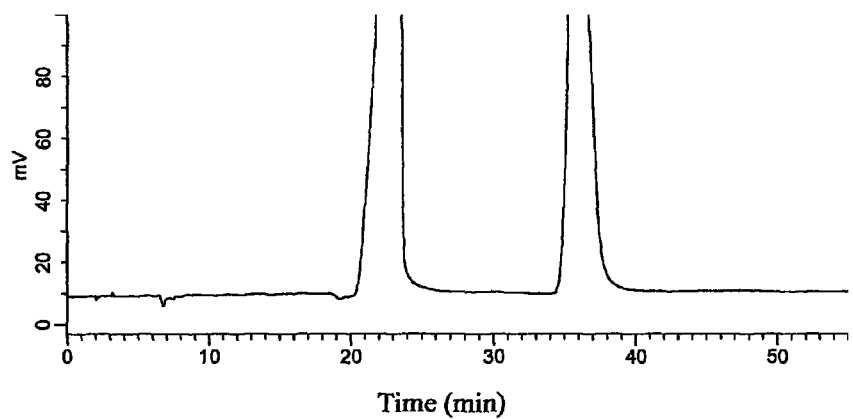
Figure 3:
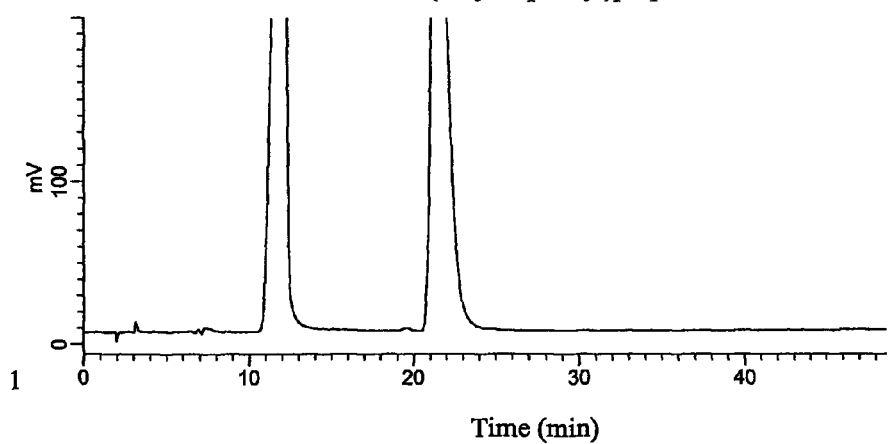

Table 4 summarizes the results. FIG. 3 shows the chromatographic resolution of optical isomers of different β-amino acids using the separating columns according to Example 3.

TABLE 4

| Substance | k'₁ | k'₂ | α | R_s |
|---|---|---|---|---|
| 3-Amino-3-(4-chlorophenyl)-propionic acid | 15.43 | 25.10 | 1.63 | 5.44 |
| 3-Amino-3-(3-methoxyphenyl)-propionic acid | 6.72 | 10.95 | 1.63 | 5.13 |
| 3-Amino-(4-cyanophenyl)-propionic acid | 3.04 | 6.13 | 2.02 | 6.03 |
| 3-Amino-3-thiophen-2-yl-propionic acid | 2.37 | 4.10 | 1.73 | 3.38 |
| 3-Amino-3-(2-chlorophenyl)-propionic acid | 10.88 | 36.3 | 3.34 | 10.6 |
| 3-Amino-3-(3-chlorophenyl)-propionic acid | 15.41 | 24.50 | 1.59 | 4.94 |
| 2-Hydroxy-2-phenylacetic acid | 10.81 | 13.81 | 1.28 | 1.26 |
| 2-Amino-3-phenylpropionic acid | 14.61 | 26.92 | 1.84 | 2.75 |
| 3-Amino-3-phenylpropionic acid | 3.16 | 5.44 | 1.72 | 5.08 |
| 3-Amino-3-(4-fluorophenyl)-propionic acid | 4.14 | 6.54 | 1.58 | 5.57 |
| 3-Amino-3-(3-fluorophenyl)-propionic acid | 4.87 | 7.41 | 1.52 | 4.10 |

Mobile Phase: 0.1 mM copper(II) acetate solution/methanol (900 + 100, v/v), flow rate: 1 ml/min, temperature: 30° C.

Numerous modifications and variations on the present invention are possible in light of the above teachings. It is therefore to be understood that within the scope of the appended claims, the invention may be practiced otherwise than as specifically described herein.

The invention claimed is:

1. A stationary phase for chromatographic separation, comprising
   a support material, and
   a chiral selector covalently attached to the support material;
   wherein
   the support material comprises silica gel or a monolith, and
   the chiral selector comprises: an α-unsubstituted β-amino acid derivative of structure (I):

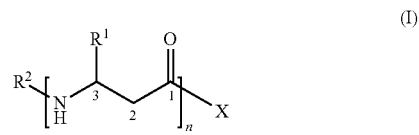

wherein
n is an integer of 1-5,
$R^1$ is —$(C_6$-$C_{10})$-aryl, $(C_7$-$C_{13})$-aralkyl, $(C_7$-$C_{10})$-heteroaralkyl, pyridyl,
X is a linking group covalently attached to the support material,
$R^2$ is 3,5-dinitrobenzoyl or naphthyl, and
the chiral selector is present in predominantly one absolute configuration with respect to the C-3 carbon atom (β-carbon atom).

2. The stationary phase for chromatographic separation according to claim 1, wherein $R^1$ is phenyl.

3. The stationary phase for chromatographic separation according to claim 1, wherein X is an aminoalkyl linker and the chiral selector is bonded to the support material as a carboxamide formed of the C1 carbon and amine nitrogen of the aminoalkyl linker.

4. A process for chromatographically separating a substance mixture, comprising:
contacting a solution of the substance mixture to be separated with the stationary phase for chromatographic separation according to claim 1;
passing a mobile phase through the stationary phase to effect separation of mixture components on the basis of their different interaction with the stationary phase, and optionally,
isolating the separated components from the mobile phase, detecting the separated components or detecting and quantifying the components;
wherein
the substance mixture comprises a mixture of chiral substances.

5. The process for chromatographically separating a substance mixture according to claim 4, wherein the substance mixture comprises trace amounts of enantiomers.

6. The process for chromatographically separating a substance mixture according to claim 5, wherein the enantiomers comprise enantiomers of α- and β-amino acids.

7. A high pressure liquid chromatography process comprising:
contacting a solution of the substance mixture to be separated with the stationary phase for chromatographic separation according to claim 1;
passing a mobile phase through the stationary phase to effect separation of mixture components on the basis of their different interaction with the stationary phase;
detecting the separated components; and
quantifying the components;
wherein the substance mixture comprises enantiomers of at least one material selected from the group consisting of α-amino acids, β-amino acids, α-hydroxy acids and derivatives thereof.

* * * * *